(12) United States Patent
Gargiulo et al.

(10) Patent No.: US 8,652,063 B2
(45) Date of Patent: Feb. 18, 2014

(54) NON-INVASIVELY MEASURING PHYSIOLOGICAL PROCESS

(75) Inventors: Gaetano Gargiulo, Monterey (AU); Jonathan Craig Tapson, Winmalee (AU); Richard William Shephard, Maffra (AU)

(73) Assignee: Heard Systems Pty Ltd, Sydney (AU)

( * ) Notice: Subject to any disclaimer, the term of this patent is extended or adjusted under 35 U.S.C. 154(b) by 0 days.

(21) Appl. No.: 13/382,877

(22) PCT Filed: Jul. 5, 2010

(86) PCT No.: PCT/AU2010/000853
§ 371 (c)(1),
(2), (4) Date: Jan. 6, 2012

(87) PCT Pub. No.: WO2011/003132
PCT Pub. Date: Jan. 13, 2011

(65) Prior Publication Data
US 2012/0108989 A1    May 3, 2012

(30) Foreign Application Priority Data
Jul. 6, 2009    (AU) .............................. 2009903169

(51) Int. Cl.
*A61B 5/0444*    (2006.01)
*A61B 5/0205*    (2006.01)

(52) U.S. Cl.
USPC ........................... 600/508; 600/453; 600/511

(58) Field of Classification Search
USPC ........................................ 600/453, 508, 511
See application file for complete search history.

(56) References Cited

U.S. PATENT DOCUMENTS

| 3,703,168 | A | * | 11/1972 | Frink | 600/511 |
| 4,256,118 | A | * | 3/1981 | Nagel | 600/546 |
| 4,700,711 | A | * | 10/1987 | Carlson | 600/449 |
| 4,898,179 | A | * | 2/1990 | Sirota | 600/483 |
| 5,042,499 | A | * | 8/1991 | Frank et al. | 600/511 |
| 5,509,421 | A | * | 4/1996 | Muller et al. | 600/437 |
| 6,171,263 | B1 | | 1/2001 | Sullivan | |

(Continued)

FOREIGN PATENT DOCUMENTS

| EP | 1 844 706 A1 | 10/2007 |
| GB | 2 162 644 A | 2/1986 |

(Continued)

OTHER PUBLICATIONS

International Search Report and Written Opinion of corresponding PCT/AU2010/000853, dated Sep. 20, 2010, 16 pages.

(Continued)

*Primary Examiner* — Niketa Patel
*Assistant Examiner* — Christopher A Flory
(74) *Attorney, Agent, or Firm* — Christie, Parker & Hale, LLP

(57) ABSTRACT

Equipment (10) for non-invasively measuring a physiological process includes at least one receiver (12) to be placed relative to a body of a subject being examined to detect at least one signal from the body of the subject. A discrimination unit (20.1) determines if the at least one signal is a signal of interest associated with the physiological process. A processor (20) processes the signal of interest to enhance the signal of interest and suppresses other received signals that are not of interest.

28 Claims, 2 Drawing Sheets

(56) References Cited

U.S. PATENT DOCUMENTS

| | | | |
|---|---|---|---|
| 6,340,346 B1 | 1/2002 | Almog et al. | |
| 6,658,284 B1* | 12/2003 | Rosen et al. | 600/511 |
| 6,751,498 B1* | 6/2004 | Greenberg et al. | 600/511 |
| 7,470,232 B2* | 12/2008 | Hoctor et al. | 600/453 |
| 7,532,923 B1* | 5/2009 | Hayes-Gill et al. | 600/511 |
| 8,175,692 B2* | 5/2012 | Kimura et al. | 600/511 |
| 2002/0193670 A1* | 12/2002 | Garfield et al. | 600/304 |
| 2004/0243015 A1* | 12/2004 | Smith et al. | 600/511 |
| 2005/0267377 A1* | 12/2005 | Marossero et al. | 600/511 |
| 2006/0241425 A1* | 10/2006 | Payne | 600/437 |
| 2007/0233203 A1* | 10/2007 | Euliano et al. | 607/46 |
| 2007/0255122 A1* | 11/2007 | Vol et al. | 600/301 |
| 2008/0125668 A1* | 5/2008 | Graupe et al. | 600/511 |
| 2008/0146953 A1* | 6/2008 | Kimura et al. | 600/511 |
| 2008/0269625 A1* | 10/2008 | Halperin et al. | 600/508 |
| 2009/0192396 A1* | 7/2009 | Hayes-Gill et al. | 600/511 |
| 2009/0259133 A1* | 10/2009 | Wolfberg et al. | 600/511 |
| 2012/0083676 A1* | 4/2012 | Wolfberg et al. | 600/301 |

FOREIGN PATENT DOCUMENTS

| | | |
|---|---|---|
| WO | WO 00/54650 | 9/2000 |
| WO | WO 01/26545 A1 | 4/2001 |
| WO | WO 2004/016163 A1 | 2/2004 |
| WO | WO 2006/025055 A2 | 3/2006 |
| WO | WO 2006/081447 A2 | 8/2006 |

OTHER PUBLICATIONS

Abboud, et al., "An Improved Detection Algorithm in Fetal Electrocardiography," Journal of Electrocardiology, vol. 22 Supplement, 1989, pp. 238-242.

Kotas, et al., "Detection of Low Amplitude Fetal QRS Complexes," 30th Annual International IEEE EMBS Conference, Aug. 20-24, 2008, pp. 4764-4767.

Saini, et al., "Computerized Detection of Low-Level Fetal Signals in the Maternal Abdominal Electrocardiogram," Comput. Biol. Med., vol. 15, No. 2, 1985, pp. 81-93.

Flynn, "Noninvasive Monitoring," The Journal of Anesthesiology, vol. 37, No. 3, Sep. 1972, pp. 265-267.

Kintraia, et al., "Development of daily rhythmicity in heart rate and locomotor activity in the human fetus," Journal of Circadian Rhythms, vol. 3, No. 5, Mar. 31, 2005, pp. 1-12.

Extended European Search Report for corresponding European Patent Application No. 10 79 6575.8, mailed Jun. 17, 2013, 6pp.

* cited by examiner

NON-INVASIVELY MEASURING PHYSIOLOGICAL PROCESS

CROSS-REFERENCE TO RELATED APPLICATIONS

This application is a national phase application under 35 U.S.C.§371 of International Application No. PCT/AU2010/000853 filed on Jul. 5, 2010, which claims the benefit of Australian Provisional Patent Application No. 2009903169, filed on Jul. 6, 2009, the disclosures of both of which are incorporated herein by reference in their entirety.

FIELD

The present disclosure relates, generally, to the non-invasive measurement of a physiological process such as, but not limited to, the detection of foetal heart (cardiac) and/or pregnant uterus signals through interposed maternal tissue. More particularly, the disclosure relates to a method of, and equipment for, non-invasively measuring a physiological process which can be used, inter alia, for detecting foetal cardiac activity and/or the presence of a pregnant uterus to allow an operator to determine the pregnancy status of the female, the stage of pregnancy, the number of foetuses present within the pregnancy and the health of the foetuses.

BACKGROUND

The applicants are aware of various methods for determining pregnancy status, the number of foetuses present and the stage of pregnancy within females (animals and humans). The methods that are used may be divided into two broad categories; physical detection of the foetus and/or pregnant uterus and laboratory-based methods for detecting chemical and/or hormonal changes within the female that are associated with pregnancy.

Physical methods include the manual palpation of the foetus and pregnant uterine structures by an experienced operator. In humans this service is typically provided by medical practitioners and in animals by veterinary surgeons. For example, in cattle, the foetus along with changes to the uterine environment associated with pregnancy can be manually detected by per rectum palpation of the uterus and its contents from around 35 days of pregnancy by an experienced operator. Larger animals (such as horses and cattle) are amenable to per rectal manual palpation of the uterine contents and uterine environment and, as such, pregnancy may be detected at an earlier stage than for animals that cannot be submitted to this process (e.g. humans, dogs, cats, sheep, pigs).

Manual palpation in larger animals by experienced operators allows accurate aging of the stage of pregnancy but is not capable of reliable detection of multiple pregnancies. External palpation of the uterus and uterine environment (through the body wall of the mother) may allow detection of pregnancy; but at a later stage of pregnancy and at lower sensitivity than is possible using internal palpation based methods. The operator skill required to undertake accurate palpation-based pregnancy diagnosis is extensive and the process is often limited by law to veterinarians or medical practitioners within many jurisdictions.

Another physical method for pregnancy detection is the use of ultrasound (US) to detect the presence of a foetus and/or changes to the uterine environment associated with pregnancy (including size, fluid content and blood flow). Ultrasound-based methods transmit high frequency sound waves towards structures under examination and record reflected sound waves. These reflected waves are processed and usually converted to visual images for assessment by the operator.

One of the US methods employed is two-dimensional real time US which uses a transducer array to create an image of the structures within the projected (and reflected) sound beam. This method requires skill to direct the transducer to the appropriate site, to exclude interposed air pockets and to interpret signal and images that are obtained.

Another US method is RT-Mode US which allows identification of foetal age, the presence of foetal death, multiple foetuses (i.e. litters) and sexing of foetuses. High frequency transducers are needed to visualise delicate uterine and foetal structures. These higher frequencies are characterised by poor tissue penetration, necessitating close internal positioning of the probe and highly skilled operators.

A (Amplitude)-Mode US uses a reflected sound wave to determine the depth of tissue structures below the probe. Again, significant skill is required to move the device into the appropriate position and to interpret the output.

B (Brightness)-Mode US is similar to A mode ultrasound except the reflected sound wave is converted to light of an intensity that mimics the amplitude of the reflected sound. A- and B-Mode US methods have been described in pregnancy diagnosis in animals.

M Mode US uses a single beam of sound and the reflected signal is used to update a visual presentation of movement of the interfaces between surfaces continually. The frequency of transmitted sound waves is typically very high and therefore this method is useful to visualise rhythmic movements (e.g. the heart) and for assessing size of structures. M mode is used extensively in human cardiac and foetal cardiac imaging.

Doppler US measures the change in frequency that occurs when transmitted sound waves are reflected from moving surfaces (or fluids). This change in frequency is converted to an audible signal that the operator may use to identify movement (such as due to the presence of a foetus). The foetal heart and circulatory movement can be detected with this method along with changes to maternal uterine blood flow as blood flow increases to meet foetal and placental demand. Doppler US probes must be directed against the structure in question and at an angle that is not perpendicular to the plane of movement. As such, reasonable skill is required to produce a diagnostic signal. Doppler US allows identification of multiple foetuses (e.g. the detection of multiparous pregnancies and estimated litter size). Doppler US has not proved reliable in pigs or cattle pregnancy diagnosis being associated with low sensitivity.

Another potential physical detection method for pregnancy diagnosis is the electrocardiogram (ECG). An ECG has been used to record foetal heart activity with detection of the bovine foetal heart from 150 days of pregnancy reported. Detection time can be slow (one study reporting between 3-5 minutes to obtain a recording from pregnant cows in the second half of gestation) as the raw signal must be visually examined for presence of foetal heart activity. Sensitivity of the method is not optimal but the method can reliably detect multiple pregnancies in cattle and horses.

The foetal ECG signal from external leads applied to the mother in late pregnancy in cattle is around 10 µV and significant electrical noise from the farm environment (e.g. from milking machines, electrical fences, etc.) is often present. A study in horses found the variability in signal strength arising from different lead positions and the numerous lead configurations to be the greatest challenge to the use of ECG. The study also found great variability in foetal heart rate in horses; in contrast to cattle. Other studies have found equine foetal heart rate monitoring using ECG successful but time consuming to obtain. Twin foetuses are readily detected using external ECG in horses. Electrode attachment to the skin of the mother is not without risk. The abdominal electrode especially is resented by many mares necessitating movement to a more lateral position, away from the ventral midline.

The maternal ECG of dairy cows may also experience changes associated with pregnancy. A standard six-limb ECG identified two significant findings: (1) for lead II, the T-wave is negative for most pregnant cows and positive for non-pregnant cows and (2) pregnant cows generally demonstrate a right axis deviation in the mean electric axis when compared to non-pregnant cows (i.e. no axis deviation).

Laboratory-based analytical methods of pregnancy diagnosis require the collection of a diagnostic sample obtained from the mother (e.g. blood, urine, milk, faeces). The sample is analysed to determine the presence of or level of a specific hormone or chemical (metabolite) that is correlated to pregnancy status and, for some, to the stage of the pregnancy. These methods require significant efficiencies in sample collection, identification, processing and reporting to minimise time lag and identification errors. Many are intrusive, requiring invasive sample collection (e.g. blood). Many assays require laboratory support and/or prolonged sample processing time and are therefore not able to provide a diagnosis to the operator within a few minutes of collection of the sample. This lack of timeliness prevents immediate processing of animals based upon pregnancy result and necessitates at least two collection, handling and processing events for the livestock. Many assays are expensive and therefore are not practical for commercial farm animals. Sample-based systems are also prone to transcription errors—especially for tests requiring more than one livestock processing event. There are numerous laboratory sample-based methods for diagnosing pregnancy. None has the necessary accuracy, convenience, timeliness of diagnosis and cost effectiveness for commercial use on animals. All require either use of laboratories or prolonged field processing times meaning that results are not available in real time. Many assays measure compounds that persist for prolonged periods (up to 100 days) after birth making the assessment of subsequent pregnancies difficult and thereby reducing specificity.

The disadvantages of existing methods of pregnancy diagnosis are many. Manual-based methods require significant operator skill and often make use of expensive equipment. As such, these diagnostic methods are typically provided by contractors on a fee-for-service basis. Often the supply of contractors is limited within regions (and in many jurisdictions supply is limited by acts of law to medical practitioners and veterinarians). Manual-based methods may also present a risk to the unborn foetus, the animal and the operator. Laboratory-based methods also require sample collection and this can be invasive, inconvenient and expose the animal to risk (infection, haemorrhage). Most assay-based methods do not provide a diagnosis in real time and are costly.

To the best of the Applicants' knowledge, all existing forms of pregnancy diagnosis either require access to expertise and/or specialised equipment thereby limiting their convenience. Many require a time delay (assay-based testing) and all are associated with ongoing costs. Given the current constraints, most pregnancy diagnosis of farms animals is therefore performed on batches of animals when the cost of intervention can be spread across more than one individual. Very rarely are single animal diagnoses sought resulting in delayed testing of individuals.

SUMMARY

A method of non-invasively measuring a physiological process includes:

placing at least one receiver relative to a body of a subject being examined and using the at least one receiver to detect at least one signal from the body of the subject;

determining if the at least one signal is a signal of interest associated with the physiological process; and pre-processing the signal of interest to enhance the signal of interest and to suppress other received signals that are not of interest.

The method has particular application in the detection of pregnancy in domestic animals. It will, however, be appreciated that the method is equally applicable in the detection of pregnancy in humans as well as other animals such as pets, wild animals, etc. Thus, the physiological process to be measured may be the presence of a foetal cardiac signal and embodiments will be described with reference to that application below.

The method may therefore include determining the presence of foetal cardiac signals (including but not limited to auditory, kinetic, and electrical signals) within naturally radiated signals obtained from the placement of one or more receivers against or near the body of the subject being examined, i.e. the female whose maternal condition is to be determined.

The method may include detecting the presence of one or more cardiac signals by determining if periodic repetitions at a rate consistent with a foetal heart rate (about 50-300 beats per minute) occurs.

The method may include, once the presence of one or more cardiac signals has been detected, determining if a foetal cardiac signal is present. The method may include determining from the receiver data that there is more than one cardiac signal present and, if more than one cardiac signal at different rates is found in the receiver data, confirming pregnancy of the subject.

The method may include, if only one cardiac signal is detected, determining if the detected signal is maternal or foetal. Thus, the method may includes measuring the maternal heart rate separately. The method may include measuring the maternal heart rate by at least one of (a) applying the at least one receiver to a region where the maternal cardiac signal is known to be strong and foetal cardiac signals are known to be absent or weak and (b) measuring the maternal heart rate by means other than the use of the at least one receiver, such as by using a stethoscope.

The method may include processing the received signals to determine signal quality. The method may include monitoring and evaluating variations in signal quality in real time and feeding data relating to the signal quality back to an operator to allow, if necessary, remedial action to be taken to improve the signal quality.

Further, the method may include, once the data have been obtained, automating a task of diagnosing the presence of a foetal cardiac signal using at least one predetermined technique. These techniques may include: (a) classical statistics, such as analysis of signal amplitude and power distributions; (b) digital signal processing, which include time-domain and frequency-domain methods such as auto- and cross-correlation, (c) spectral and cepstral analysis, (d) separation of components (blind source separation) by means of methods such as independent component analysis or principal component analysis, (e) pattern recognition and data clustering that are used to find a desired signal component in signal noise and clutter, (f) neural networks and kernel methods (such as support vector machines), (g) the use of heuristics—"rules of thumb" which help to interpret the data, such as might be applied by a human data interpreter, or the like. The method may include using a number of the techniques in parallel.

The method may include effecting pre-processing enhancement of interest, in the form of some kind of filtering, prior to applying the at least one technique. The method may include effecting pre-processing enhancement of the signal by using a combination of low-pass, band-pass, and high-pass filtering.

The method may include combining outputs of the applied techniques, using a classifier, to make a final decision. The classifier, sometimes called a "committee of experts", may use methods such as Bayesian statistics to allocate a weight or importance to the outcome, based upon the signal quality, the known reliability of the method, and a knowledge of prior probabilities of accuracy.

The method may include further outputting, as part of the decision, data relating to a measure of confidence in the decision which may be of use in the business or agricultural health context in which the diagnosis is taking place.

The method may include combining historical data with data obtained from the a least one receiver to produce an updated estimate of pregnancy status, number of foetuses, foetal age and predicted time until parturition for a number of subjects being investigated. The historical data may include, but is not limited to, female electronic animal identification data, management and production data and previous pregnancy diagnosis data.

Further, the method may include transferring multi-field data in a format suitable for inclusion with computer software.

Equipment for non-invasively measuring a physiological process includes:

at least one receiver to be placed relative to a body of a subject being examined to detect at least one signal from the body of the subject;

a discrimination unit for determining if the at least one signal is a signal of interest associated with the physiological process; and a processor for processing the signal of interest to enhance the signal of interest and to suppress other received signals that are not of interest.

The equipment may include a receiver pack comprising a plurality of receivers operable to detect different types of signals. The receiver pack may include at least some of the following types of receivers:

at least one audio receiver for receiving sound wave information from the subject being examined;

at least one electrical receiver, each of which may comprise an electrode, for receiving muscle and nerve electrical activity signals from the subject being examined; and at least one pressure receiver, including an accelerometer, for receiving kinetic information from the subject being examined.

The processor may be in communication with the receiver pack for processing the received signals, performing computations to enhance the signal of interest and to filter noise and other signals not of interest to provide refined signals. The processor may employ algorithms to interpret the refined signals, optionally combine the refined signals with historical data and provide an output in the form of information on the physiological process. As indicated above, the physiological status in the preferred application of the equipment is the detection of a pregnancy status of a female domestic animal, the likely number of foetuses present, the estimated age of the pregnancy and the estimated time to parturition.

The discrimination unit may comprise a pre-processing module for effecting pre-processing of the signal of interest. The pre-processing module may use a combination of low-pass, band-pass and high-pass filtering.

The processor may include an evaluation module for monitoring and evaluating variations in signal quality in real time. The equipment may include an enunciator for alerting an operator to the signal quality.

The processor may be configured to automate a task of diagnosing the presence of a foetal cardiac signal using at least one predetermined technique. The processor may be configured to use a number of the techniques in parallel.

The processor may include a classifier which is operable to combine outputs of the applied techniques to make a final decision about the signal of interest. Further, the processor may be configured to output, as part of the decision, data relating to a measure of confidence in the decision.

The equipment may include a data storage system for recording and accessing data from multiple animals and events.

To enable the equipment to be used in the field, the equipment may include a portable power supply.

The equipment may include a data input and processing system for combining historical and current data including, but not limited to, female electronic animal identification data, management and production data and previous pregnancy diagnosis data for concurrent processing and output. The processor may be operable to combine, analyse and interpret serially obtained foetal cardiac signals from individual females with the currently obtained signal to produce an updated estimate of pregnancy status, number of foetuses, foetal age and predicted time until parturition using all combined information.

Still further, the equipment may include an output system for transferring multi-field data in a format suitable for inclusion with computer software.

BRIEF DESCRIPTION OF DRAWINGS

Embodiments are now described by way of example with reference to the accompanying drawings in which:—

DETAILED DESCRIPTION OF EXEMPLARY EMBODIMENT

Figure 1:
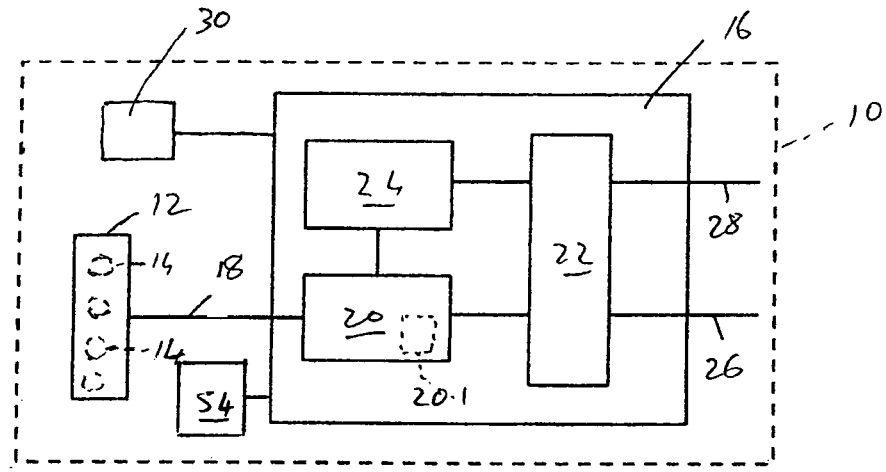
FIG. 1 shows a block diagram of an embodiment of equipment for non-invasively measuring a physiological process.

In FIG. 1 of the drawings, reference numeral 10 generally designates an embodiment of equipment for non-invasively measuring a physiological process. The equipment 10 has particular application in the detection of pregnancy in domestic animals and, more particularly, in animals used in animal husbandry such as cattle, sheep, pigs or horses. The equipment will be described with reference to that application but those skilled in the art will readily appreciate that the equipment, and associated method, could be used in other applications where rapid, cost effective, early detection of pregnancies is desirable. The equipment and method can also be used in the detection of pregnancy in humans.

The equipment 10 is used for recording and processing of passively received foetal cardiac signals. A "passively received" signal is one which is naturally radiated from the animal's body as opposed to a signal generated by an actuator such as would occur with ultrasound techniques. These naturally radiated cardiac signals include, but are not limited to, audio signals, electrical signals, kinetic signals and physiological signals.

The equipment 10 includes a receiver pack 12. The receiver pack 12 comprises a plurality of receivers or sensors 14. The sensors 14 are electrodes able to be placed relative to the animal without any preparatory work being done on the animal's body. Examples of such electrodes are disclosed in the applicant's co-pending International Patent Application No. PCT/AU2009/000873 dated 6 Jul. 2009 and entitled "A system for sensing electrophysiological signals".

The sensors 14 of the receiver pack 12 are placed against or near the body of a subject being examined, for example, a pregnant cow. The sensors 14 are used to capture signals radiated from the body of the animal in question. As indicated above, theses sensors can be used to capture audio, kinetic and electrical signals passively.

The equipment 10 includes a processor in the form of a data processing unit 16 to which the receiver pack 12 is connected via a cable 18. It will be appreciated that, instead, the receiver pack 12 could communicate wirelessly with the processor 16. Further, the receiver pack 12 and the data processing unit 16 are preferably contained together in a portable unit.

The processor 16 includes a signal processor 20 which processes signals output by the sensors 14 of the receiver pack 12. The processor 16 further includes a microprocessor 22 which controls operation of the signal processor 20 as well as a data storage unit 24 in which data relating to the animals being tested are stored.

The equipment 10 further includes an output data port 26 and an input data port 28.

To enable the equipment 10 to be used in the field, the equipment 10 also includes a power supply 30 so that the equipment 10 is portable. For example, the power supply 30 is a battery powered power supply using re-chargeable batteries.

As indicated above the equipment 10 is a low-cost device for detection of pregnancies in domestic animals. In addition to determining whether or not an animal is pregnant, the equipment 10 can be used to provide an indication of the number of foetuses being carried by the animal, the foetal age and the predicted time until parturition. It is also envisaged that the equipment 10 can be used in a rapid manner so that a number of animals can be tested at any one time in rapid succession.

Thus, in use, the sensors 14 are placed on and/or in proximity to the animal's body. For example, in the case of a portable unit, the sensors 14 may be arranged in an array on the face of the unit. The face of the unit is then placed against the animal's body. The sensors 14 detect signals of different types associated with the animal being investigated such as audio, electrical, kinetic and physiological signals. The signals detected by the sensors 14 are fed to the signal processor 20 where the detected signals are processed.

The signal processor 20 includes a pre-processor 20.1 in the form of discrimination unit for determining if at least one signal of interest is present. A signal of interest is a signal associated with a heartbeat of a foetus carried by the animal.

The discrimination unit 20.1 of the signal processor 20 makes use of a combination of low-pass filters, band-pass filters and high-pass filters. In addition, the discrimination unit of the signal processor 20 uses more advanced signal extraction techniques such as blind source separation.

Figure 2:
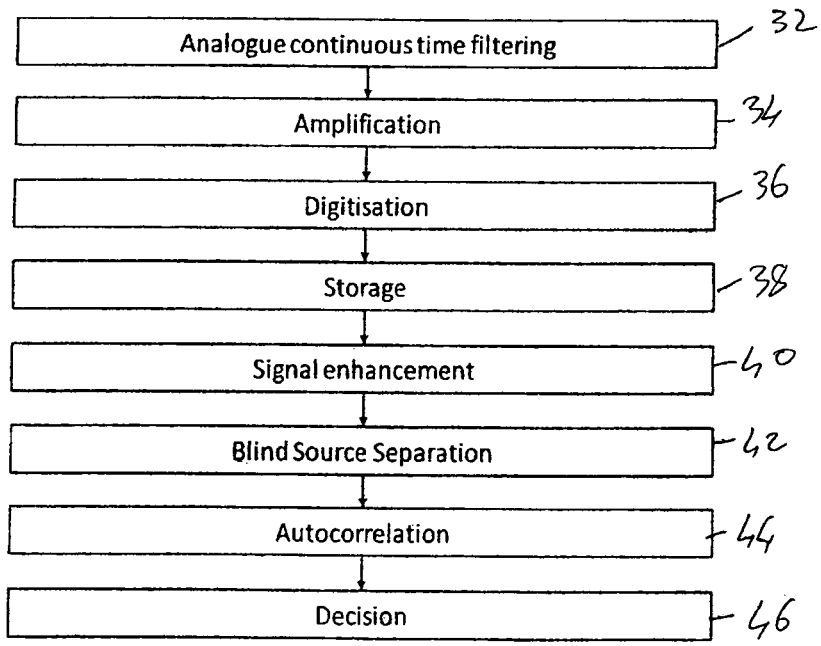
FIG. 2 shows a flow chart of steps used by a component of the equipment of FIG. 1 for carrying out an embodiment of a method of non-invasively measuring a physiological process.

The steps employed by the signal processor 20 of the equipment 10 are shown in FIG. 2 of the drawings. More particularly, at step 32, the received signals from the sensors 14 of the receiver pack 12 are filtered using analog, continuous time filters to limit the signal to the frequency range of interest, the frequency range being approximately 2 Hz-200 Hz. At step 34, the filtered signals are amplified as much as possible using an amplifier of the signal processor 20 but taking care to ensure that the maximum signal excursion remains within the range of an analogue to digital converter used.

At step 36, the analogue signals are digitised using an analogue to digital converter to obtain digitised sensor data. The digitised sensor data are stored in the memory 24 for a recording period of at least several seconds at step 38.

The signal processor 20 processes the stored sensor data by applying matched filters to enhance the detection of individual heartbeats from the signals detected by the sensors 14 of the receiver pack 12. The signal from each sensor 14 will contain a mixture of signals from different sources such as, for example, the maternal heartbeat, a foetal heartbeat, if present, muscular contractions and other noise signals. Thus, at step 40 signal enhancement is carried out by the signal processor 20. A blind source separation technique is used at step 42 to extract signals belonging to the various sources. An example of a blind source signal separation technique used is independent component analysis. Each source signal is checked for periodicity using an auto-correlation analysis at step 44.

If the signal is periodic with a rate between about 30 beats per minute (BPM) and 300 BPM, it is classified as a heartbeat signal. It is to be noted that this range is applicable to larger animals such as cows and will be different for smaller animals such as sheep or pigs.

If two or more separate heartbeat signals are detected, a decision of "pregnant" is registered at step 46. If only one heartbeat signal is detected and this heartbeat signal is periodic with a rate between about 120 BPM and 300 BPM, it is likely that a single foetal heartbeat from a healthy foetus has been detected. A retest may then take place with at least one of the sensors 14 closer to the heart of the animal being examined to confirm the pregnancy status. Conversely, if only one heartbeat signal is detected in the range of about 30 BPM and 120 BPM a "non-pregnant" decision is rendered.

Detected heart rates outside this range may indicate the presence of a foetus of unknown health status and a retest at a future stage is recommended.

Figure 3:
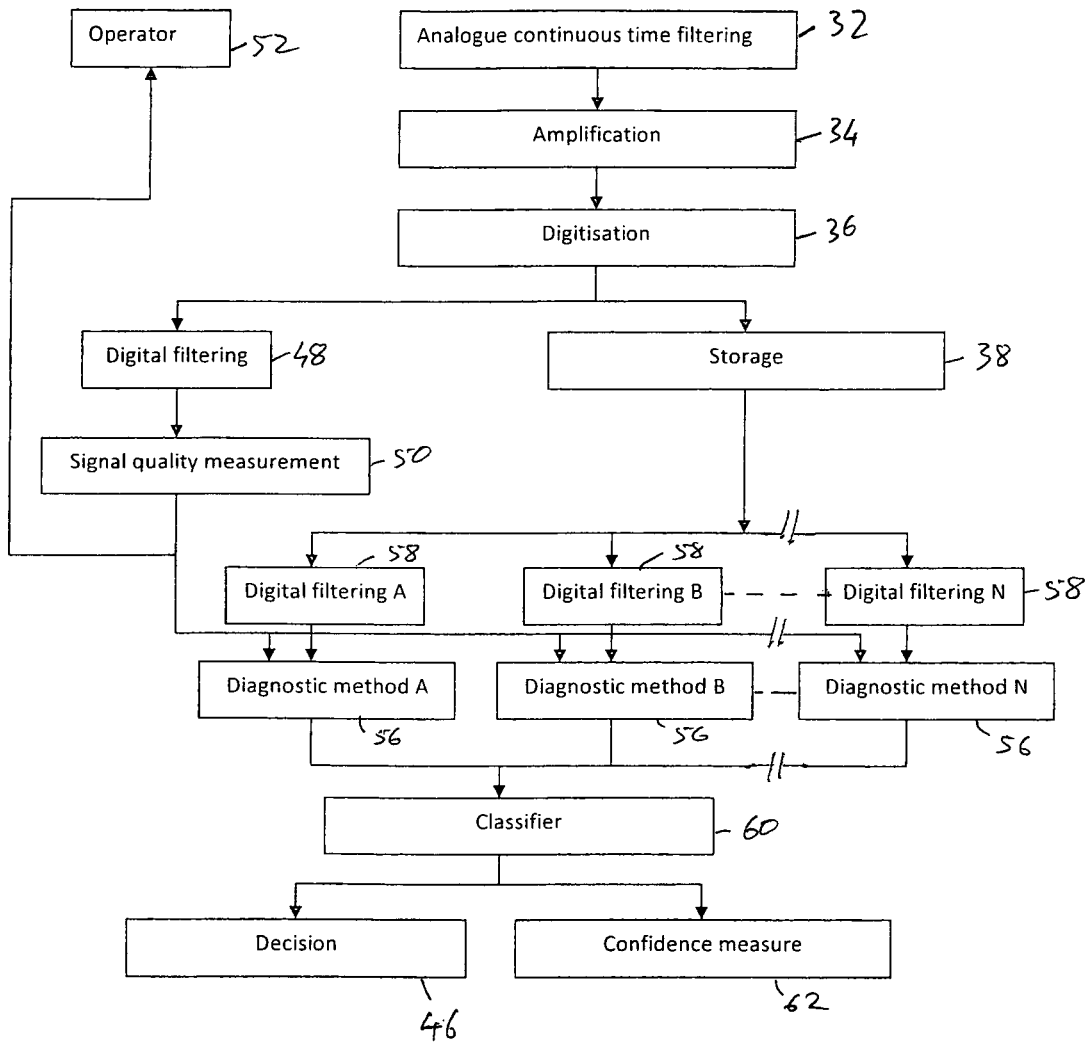
FIG. 3 shows a flow chart of steps used by a component of the equipment of FIG. 1 for carrying out another embodiment of a method of non-invasively measuring a physiological process.

Referring now to FIG. 3 of the drawings, a further embodiment of the operation of the signal processor 20 is now described: With reference to FIG. 2, like reference numerals refer to like steps unless otherwise specified.

As in the case of FIG. 2, steps 32-38 are the same. In this embodiment, however, the incoming digitised signal is assessed by the signal processor 20 for signal quality.

At step 48, the signal is subjected to digital filtering and, at step 50, the filtered signal is processed to derive a measure of signal quality. Given that the subjects of the method may well be animals, such as cattle, which cannot practically be immobilised or anaesthetised, and which may be kept in an open-air environment which is inhospitable to electronic measurement systems, the application of the sensors 14 is likely to be highly variable, with a consequential variation in signal quality. This variation is measured and evaluated in real time and data relating to signal quality are fed back to an operator, as indicated at 52. For this purpose, the equipment 10 includes an enunciator 54 for indicating the signal quality to the operator. The enunciator 54 may be an audible and/or visual device. For example, the enunciator 54 may emit an audible alarm if the signal quality is below a required threshold or, conversely, an audible signal may be emitted if the signal quality is adequate.

In addition, or instead, the enunciator 54 may include a display for displaying a measure of the signal quality.

This allows for the immediate correction of many signal acquisition problems related to operator performance, animal behaviour or environmental interference; for example, if the animal has moved so that the sensors 14 are not making proper contact. The operator is then in a position to correct the situation immediately upon being notified via the enunciator 54.

The signal quality is analysed to detect instances where, for example, ECG electrode sensors 14 have lost contact or are in a high impedance state as a result of poor skin contact. This will result in a distinctive signal, characterized perhaps by extensive saturation or oscillation, and the operator can be informed that electrode contact is poor and the equipment 10 must be adjusted. This can be identified at the level of individual electrode sensors 14. A further type of loss of quality might be an ECG signal which is swamped by excessive electromyograph (EMG) signals arising from muscle movement in the animal close to the electrode sensors 14. In this case the operator action might be to wait until the animal settles or manage the animal in such a way as to reduce muscle movement.

The quality of the signal has a significant effect on the success of the downstream processing and diagnostics, and is a key parameter which can be used explicitly in the following diagnostic techniques or methods carried out by the signal processor 20 and as referenced at 56 in FIG. 3 of the drawings.

The diagnostic methods 56 include techniques of classical statistics, such as analysis of signal amplitude and power distributions; techniques of digital signal processing, which include time-domain and frequency-domain methods such as auto- and cross-correlation, spectral and cepstral analysis; separation of components (blind source separation) by means of methods such as independent component analysis or principal component analysis. There are also techniques of pattern recognition and data clustering that are used to find a desired signal component in signal noise and clutter and a very large number of neural networks and kernel methods (such as support vector machines) which are able to be used.

In addition, the use of heuristics—"rules of thumb" which interpret the data, such as might be applied by a human data interpreter,—assists in adding accuracy to the other methods. For example, a simple heuristic is that the maternal heart rate (of an otherwise healthy dam) should fall within a typical range, and the foetal heart rate (of an otherwise healthy foetus) should fall within a typical range, different from that of the dam, and this can help to separate the two heart rate signals.

Prior to applying the diagnostic method, the signal is preprocessed using digital filtering as shown at step 58.

It is highly unlikely that any one single method 56 will provide the most accurate diagnosis possible. Improved performance results by using several methods in parallel, as shown in FIG. 3. Each method 56 selected requires preprocessing enhancement in the form of filtering, as shown.

The outputs of these parallel diagnostic methods 56 are then combined using a classifier 60 which makes the final decision 46 on diagnosis. This classifier 60, sometimes called a "committee of experts", uses methods such as Bayesian statistics to allocate a weight or importance to the outcome, based upon the signal quality, the known reliability of the method and a knowledge of prior probabilities of accuracy.

The output of the equipment 10 is the decision 46 and a measure of confidence 62 in the decision 46 which may be of use in the business or agricultural health context in which the diagnosis is taking place is also output.

Data relating to pregnant females are output on the data output line 26. In addition, the data can be correlated with data input on the input line 28. The data input on the input line 28 may relate to historical data in regard to the herd, previous pregnancies etc. If necessary, the microprocessor 22 may process the data output on the output line 26. The data output can simply be displayed on a display (not shown) or can be modified for use with computer software and herd management devices.

It is therefore an advantage of the described embodiments that equipment 10 is provided which enables rapid, low-cost detection of pregnancy in animals in herds without the need for skilled labour to determine pregnancies. In addition, due to the non-invasive nature of embodiments of the equipment 10, little, if any, trauma is imparted to the animals being investigated.

It will be appreciated that reproductive efficiency is a major driver of financial performance of livestock enterprises. Assessing individual animal pregnancy status is key information for decision making because management requirements, maintenance costs and income potential are different for pregnant and non pregnant animals. Culling, separation, feeding and other management decisions are influenced by individual animal pregnancy status. These include, but are not limited to, determining dates for drying lactating dairy cows off, for weaning beef calves from their mothers, for culling and sale (all species), and for hastening return to mating for animals not detected as pregnant (all species). The pregnancy status of individual animals offered for sale is also often legally required information. The provision of the equipment 10 facilitates these management decisions.

Electronic individual animal identification (EID) systems are becoming more widespread within commercial animal production systems. These offer real-time point-of-contact individual animal management capability. Systems that can record data electronically, link with existing information, use algorithms to perform management decisions (eg drafting) based upon inputs are increasingly being used. The recording of pregnancy status information electronically using the equipment 10 in a manner that can link with EID provides an advantage. The simple electronic recording of pregnancy test results with animal EID reduces identification and transcription errors.

In some species, the identification of animals pregnant with more than one foetus is of great value (eg sheep, pigs and cattle). These animals can be marked for preferential treatment and management practices implemented that can optimise the pregnancy.

The reproductive performance of many farm animals is declining. Early and regular pregnancy diagnostic capability allows farmers to identify animals with superior reproductive performance. These animals may be selected to breed replacements and animals with lesser reproductive performance preferentially culled along with their offspring.

Pet animal owners and hobby farmers often want to know pregnancy status of their animals. Many pet animal veterinarians are unable to provide this service because it requires investment in expensive ultrasound equipment and extensive training in use of the machines; a cost that is difficult to recoup when demand for the service is sporadic. The availability of the equipment 10 alleviates these problems.

An accurate diagnosis of pregnancy is often required for non domesticated animals. Zoos, conservation programs, artificial mating programs and resource management systems benefit from determining the pregnancy status of individual animals. Often, specific pregnancy diagnostic laboratory-based tests do not exist for non-domesticated species. A real-time point-of-contact pregnancy test using the equipment 10 that does not require specialised skills by the operator is likely to be of great advantage to zoo staff, conservation biologists and rangers.

Whilst methods for diagnosing pregnancy are readily available for humans the provision of a personal pregnancy diagnosis and monitoring system will be appealing for individual women; especially for women at increased risk of involuntary abortion and for women from isolated regions.

Generally, the regular, early, reliable, convenient and accurate diagnosis of pregnancy of individuals using the equipment 10 assists in efficient and profitable individual farm animal management systems being deployed. In addition, an ability to undertake repeated, safe, pregnancy diagnosis confirmation will be an advantage for many women.

It will be appreciated by persons skilled in the art that numerous variations and/or modifications may be made to the disclosure as shown in the specific embodiments without departing from the scope of the disclosure as broadly described. The present embodiments are, therefore, to be considered in all respects as illustrative and not restrictive.

The invention claimed is:

1. A method of non-invasively measuring a physiological process to determine the presence of a foetal cardiac signal to detect pregnancy of a subject, the method comprising:
    placing a receiver relative to a body of the subject being examined and using the receiver to detect a plurality of signals from the body of the subject, wherein the receiver comprises a plurality of different type of sensors detecting different types of signals;
    determining whether at least one signal of the plurality of signals is a foetal cardiac signal; and
    pre-processing the at least one signal to enhance the signal and to suppress other received signals that are not of interest,
    wherein determining whether the at least one signal is a foetal cardiac signal further comprises: using a plurality of predefined techniques in parallel, combining outputs of the applied plurality of predefined techniques, using a classifier to make a final decision whether or not the signal of interest is a foetal cardiac signal; and outputting, as part of the decision, data relating to a measure of confidence in the decision.

2. The method of claim 1 further comprising determining the presence of at least one foetal cardiac signal within naturally radiated signals obtained from the placement of one or more receivers against or near the body of the subject being examined.

3. The method of claim 2 further comprising detecting the presence of one or more cardiac signals by determining whether rates of periodic repetitions are consistent with heart rates.

4. The method of claim 3 further comprising once the presence of one or more cardiac signals has been detected, determining if a foetal cardiac signal is present.

5. The method of claim 4 further comprising determining from receiver data received from the one or more receivers that there is more than one cardiac signal present and, if more than one cardiac signal at different rates is found in the receiver data, confirming pregnancy of the subject.

6. The method of claim 3 further comprising if only one cardiac signal is detected, determining whether the detected signal is maternal or foetal.

7. The method of claim 6 further comprising measuring a maternal heart rate separately.

8. The method of claim 7 further comprising measuring the maternal heart rate by at least one of (a) applying the at least one receiver to a region where the maternal cardiac signal is known to be strong and foetal cardiac signals are known to be absent or weak, and (b) measuring the maternal heart rate by means other than the use of the at least one receiver.

9. The method of claim 3 further comprising processing the received signals to determine signal quality.

10. The method of claim 9 further comprising monitoring and evaluating variations in signal quality in real time and feeding data relating to the signal quality back to an operator.

11. The method of claim 10 further comprising once the data have been obtained, automating said determination of the presence of a foetal cardiac signal using the predetermined techniques.

12. The method of claim 11 further comprising effecting pre-processing enhancement of the signal of interest prior to applying the at least one technique.

13. The method of claim 3 further comprising combining historical data with data obtained from the a least one receiver to produce an updated estimate of pregnancy status, number of foetuses, foetal age and predicted time until parturition for a number of subjects being investigated.

14. The method of claim 3 further comprising transferring multi-field data in a format suitable for inclusion with computer software.

15. The method of claim 1 further comprising effecting pre-processing enhancement of the signal of interest by using a combination of low-pass, band-pass, and high-pass filtering.

16. Equipment for non-invasively measuring a physiological process to detect pregnancy of a subject comprising:
    a receiver to be placed relative to a body of a subject being examined to detect a plurality of signals from the body of the subject, wherein the receiver comprises a plurality of different type of sensors detecting different types of signals;
    a discrimination unit for determining whether at least one signal of the plurality of signals is a signal of interest of being a foetal cardiac signal;
    a pre-processing module for pre-processing the at least one signal to enhance the at least one signal and to suppress other received signals that are not of interest;
    a processor, in communication with the pre-processing module to diagnose the presence of the foetal cardiac signal using a plurality of predefined techniques in parallel;
    a combining module controlled by the processor for combining outputs of the applied plurality of predefined techniques; and
    a classifier in communication with the combining module for making a final decision whether or not the at least one signal is a foetal cardiac signal, and outputting, as part of the decision, data relating to a measure of confidence in the decision, 17. The equipment of claim 16 further comprising a receiver pack comprising a plurality of receivers operable to detect different types of signals.

18. The equipment of claim 17 wherein the receiver pack includes at least two of the following types of receivers:
    at least one audio receiver for receiving sound wave information from the subject being examined;
    at least one electrical receiver for receiving muscle and nerve electrical activity signals from the subject being examined; and
    at least one pressure receiver for receiving kinetic information from the subject being examined.

19. The equipment of claim 17 in which the processor is in communication with the receiver pack for processing the received signals, performing computations to enhance the signal of interest and to filter noise and other signals not of interest to provide refined signals.

20. The equipment of claim 19 in which the processor employs algorithms to interpret the refined signals and provide an output in the form of information on the physiological process.

21. The equipment of claim 16 in which the discrimination unit comprises a pre-processing module for effecting pre-processing of the signal of interest.

22. The equipment of claim 16 in which the pre-processing module uses a combination of low-pass, band-pass and high-pass filtering.

23. The equipment of claim 16 in which the processor includes an evaluation module for monitoring and evaluating variations in signal quality in real time.

24. The equipment of claim 23 further comprising an enunciator for alerting an operator to the signal quality.

25. The equipment of claim 16 further comprising a data storage system for recording and accessing data from multiple subjects and events, 26. The equipment of claim 16 further comprising a portable power supply, 27. The equipment of claim 16 further comprising a data input and processing system for combining historical and current data.

28. The equipment of claim 16 further comprising an output system for transferring multi-field data in a format suitable for inclusion with computer software.

* * * * *